United States Patent [19]

Keyvani

[11] Patent Number: 5,339,712

[45] Date of Patent: Aug. 23, 1994

[54] HAND TOOL HAVING OFFSET WORK ELEMENTS

[76] Inventor: Daryoush Keyvani, 321 S. San Vicente, #302, Los Angeles, Calif. 90048

[21] Appl. No.: 143,343

[22] Filed: Oct. 25, 1993

[51] Int. Cl.$^5$ ............................................. B25B 7/00
[52] U.S. Cl. ...................... 81/416; 81/420; 81/396; 30/192; 30/257; 606/205; 433/159
[58] Field of Search ................... 81/415–420, 81/427.5, 300, 342, 358, 386, 393, 396; 30/131, 187, 188, 191–194, 245, 248–250, 252, 257, 259; 606/205, 174, 83; 433/159

[56] References Cited

U.S. PATENT DOCUMENTS

| | | | |
|---|---|---|---|
| 541,294 | 6/1895 | Smith | 30/257 |
| 1,093,726 | 4/1914 | Pearson et al. | 30/257 |
| 1,845,798 | 2/1932 | Keiser, Jr. | 30/257 |
| 2,508,805 | 5/1950 | Scott | 56/338 |
| 3,156,980 | 11/1964 | Vosbikian | 30/253 |
| 5,157,996 | 10/1992 | Keyvani | 81/416 |

FOREIGN PATENT DOCUMENTS 704090 3/1941 Fed. Rep. of Germany ...... 433/159

*Primary Examiner*—D. S. Meislin
*Attorney, Agent, or Firm*—Macro-Search Corp.

[57] ABSTRACT

A hand tool is disclosed that includes a first handle that provides at one end a first hinge joint extending in a first direction and a hollow tube extending in the other direction. A fixed work element is attached at a distal end of the tube. A second handle is aligned with the first handle and provides a second hinge joint that extends in rotational engagement with the first hinge joint and includes a first set of gear teeth facing the tube. A hinge pin is pivotally engaged with and aligns the first and second hinge joints. As such, the second handle is rotatable toward and away from the first handle about the pin. A transfer rod is rotatably held within the hollow tube and extends therethrough to a movable work element that is positioned adjacent to the fixed work element. A toothed gear segment is fixed to the transfer rod and includes a second set of gear teeth that engages the first set of gear teeth. As such, as the second handle is rotated about the hinge pin, the first set of gear teeth drive the toothed gear segment to cause the rod to rotate within the hollow tube. The movable work element thereby approaches towards, and alternately retreats from, the fixed work element. The work elements may form any of a wide variety of tools, and the hollow tube and transfer rod may be of suitable length for positioning the work elements distally from the handles.

10 Claims, 2 Drawing Sheets

HAND TOOL HAVING OFFSET WORK ELEMENTS

FIELD OF THE INVENTION

This invention relates generally to hand tools, and, more particularly, is directed towards a hand tool with offset work elements for performing work on hard-to-reach workpieces.

BACKGROUND OF THE INVENTION

Hand tools with offset work elements have been known in the prior art, and are taught in such patents as U.S. Pat. Nos. 1,845,798 to Keiser, Jr., on Feb. 16, 1932; 541,294 to Smith on Jun. 18, 1895; 1,093,726 to Pearson on Apr. 21, 1914; and my previous 5,157,996 issued on Oct. 27, 1992. The need for such tools arises when a workpiece is positioned such that it is difficult to reach or manipulate with more conventional tools due to interference from nearby objects. In the case of dentistry, for example, the structures of the mouth make it difficult to adequately work on teeth such as molars with a conventional pair of pliers. Vehicle engine work also offers many difficult-to-reach workpieces. As a result, such prior art devices were developed to allow an operator easier access to difficult-to-reach workpieces.

While such prior art tools are useful in certain applications, frequently a degree of mechanical leverage needs to be exerted on a workpiece that cannot be attained from the conventional handle arrangements found in the prior art. Further, conventional handle arrangements, such as those found on a conventional pair of pliers, often require the wrist of the user to bend at nearly a 90° angle during use, which is not only uncomfortable over an extended period of time but also reduces the amount of force that the person can exert to the tool.

None of the prior art devices with offset work elements allows for increased mechanical advantage to the user while, at the same time, providing vertically aligned handles for improved comfort of the user. The present invention fulfills these needs and provides further related advantages.

SUMMARY OF THE INVENTION

The present invention is a hand tool comprising a first handle that provides at one end a first hinge joint extending in a first direction and a hollow tube extending in the other direction. A fixed work element is attached at a distal end of the tube. A second handle is aligned with the first handle and provides a second hinge joint that extends in rotational engagement with the first hinge joint and includes a first set of gear teeth facing the tube. A hinge pin is pivotally engaged with and aligns the first and second hinge joints. As such, the second handle is rotatable alternately toward and away from the first handle about the pin. A transfer rod is rotatably held within the hollow tube and extends therethrough to a movable work element that is adjacent to the fixed work element. A toothed gear segment is fixed to the transfer rod adjacent to the second hinge joint and includes a second set of gear teeth that engage the first set of gear teeth. As such, as the second handle is rotated about the hinge pin, the first set of gear teeth drive the toothed gear segment to cause the rod to rotate within the hollow tube. The movable work element is thereby caused to approach towards, and alternately retreat from, the fixed work element. The work elements may form any of a wide variety of tools, and the hollow tube and transfer rod may be of suitable length for positioning the work elements distally from the handles.

The present invention is a tool that provides offset work elements that allows for increased visibility of the work piece, increased reach of the working elements, and mechanical advantage to the user through the arrangement of the first and second sets of gear teeth. At the same time, unlike all prior art devices the present invention provides vertically aligned handles for improved comfort of the user, and thereby allows the user to exert an increased force on the tool. Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

Figure 1:
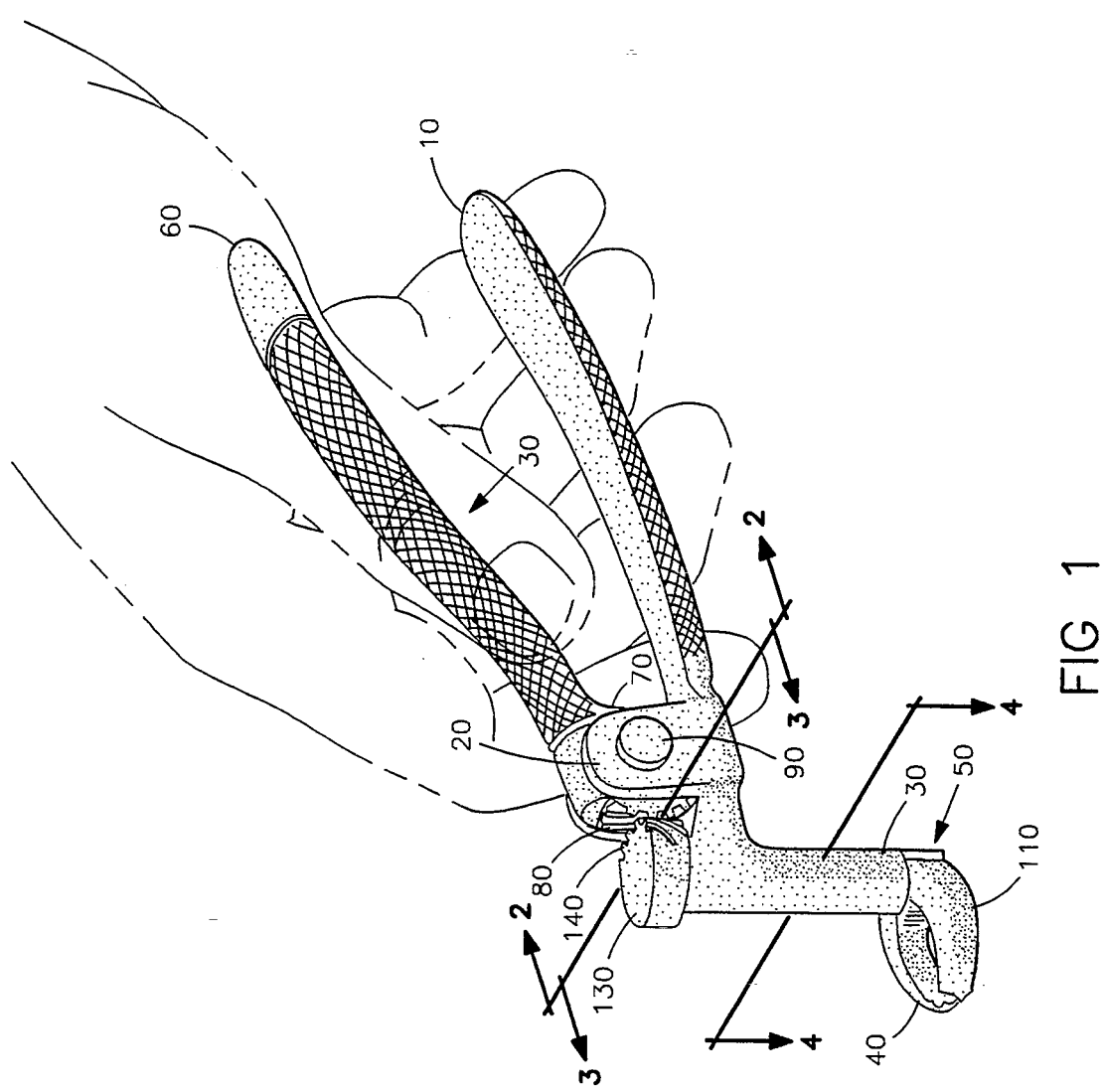
FIG. 1 is a perspective illustration of the invention, illustrating a pair of handles that rotatably drive a transfer rod within a hollow tube for moving a working element of the invention.

FIG. 1 shows a hand tool comprising a first handle 10 that provides at one end thereof a first hinge joint 20 that extends away from the handle 10 in a first direction. A hollow tube 30 extends away from the handle 10 in a direction opposite to the first direction. A fixed work element 40 is attached at a distal end 50 of the tube 30.

A second handle 60 is aligned with the first handle 10 and provides a second hinge joint 70 that extends in rotational engagement with the first hinge joint 20 and includes a first set of gear teeth 80 facing the tube 30. A hinge pin 90 is pivotally engaged with and aligns the first and second hinge joints 20,70. As such, the second handle 60 is rotatable alternately toward and away from the first handle 10 about the pin 90. The handles 10,60 are made of any suitably rigid and strong material, such as hardened steel, or the like. Further, a spring (not shown) may be positioned between each handle 10,60 to normally urge the handles 10,60 away from each other.

Figure 2:
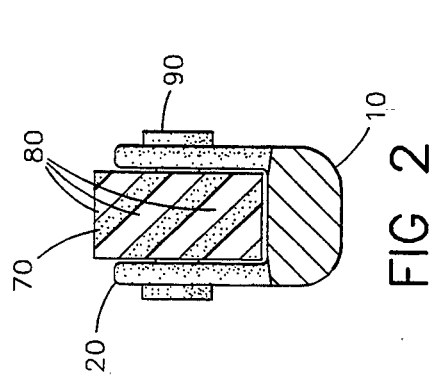
FIG. 2 is a cross-sectional view of the invention, taken along lines 2—2 of FIG. 1, illustrating a first set of gear teeth of the invention.
Figure 3:
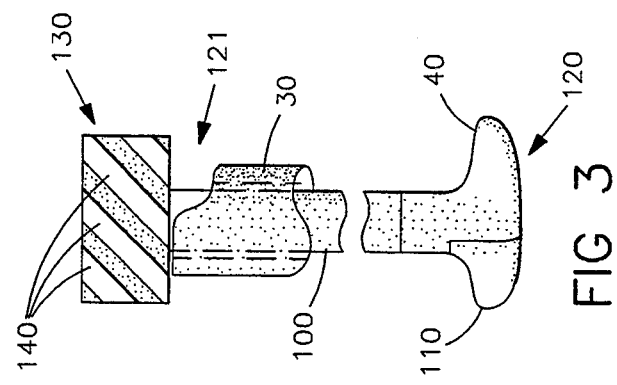
FIG. 3 is a cross-sectional view of the invention, taken along lines 3—3 of FIG. 1, illustrating a toothed gear segment and the hollow tube of the invention.

A transfer rod 100 is rotatably held within the hollow tube 30 and extends therethrough. A movable work element 110 is attached at a distal end 120 of the transfer rod 100 and adjacent to the fixed work element 40. A toothed gear segment 130 is fixed at a proximal end 121 adjacent to the second hinge joint 70 and includes a second set of gear teeth 140 that engage the first set of gear teeth 130. The toothed gear segment 130 and the movable work element 110 together hold the transfer rod 100 in the hollow tube 30. In one embodiment of the invention, the first and second gear teeth 80,140 each follow a 45° angular pattern such that action is transferred by 90° between the handles 10,60 and the work elements 40,110 (FIGS. 2 and 3). Clearly, gear teeth 80,140 may each be brass, copper, steel, or other suitably rigid and durable material.

As such, as the second handle 60 is rotated about the hinge pin 90, the first set of gear teeth 80 drive the toothed gear segment 130 to cause the rod 100 to rotate within the hollow tube 30. The movable work element 110 is thereby caused to approach towards, and alternately retreat from, the fixed work element 40. The direction of offset of the work elements 40,110 and the hollow tube 30 away from the first handle 10 is in the same plane as the motion of the second handle 60. As such, prolonged use of the present invention causes less wrist and hand fatigue, and therefore can result in a more precise effort.

In an alternate embodiment of the invention, the first set of gear teeth 80 is positioned closer to the center of rotation of the pivot pin 90 than the second set of gear teeth 140 is positioned from the center of rotation of the transfer rod 100. As such, mechanical advantage is provided to the operator. That is, the rotational travel of the second handle 60 with respect to the first handle 10 is greater than the rotational travel of the movable work element 110 with respect to the fixed work element 40. Alternatively, the first set of gear teeth 80 may be positioned further from the center of rotation of the pivot pin 90 than the second set of gear teeth 140 is positioned from the center of rotation of the transfer rod 100, thereby providing a magnification of extent of motion between the handles 10,60 and the work elements 40,110.

Similarly, the first and second gear teeth 80,140 each may follow an angle different than 45° with respect to the transfer rod 100 such that either a mechanical advantage or disadvantage is afforded to the handles 10,60. For example, instead of a gear teeth angle of 45° with respect to the transfer rod 100, such angle defining a one-to-one ratio of movement between the transfer rod 100 and the second handle 60, a gear teeth angle of 30° results in a two-to-one ratio of movement between the second handle 60 and the transfer rod 100. That is to say, with a gear teeth angle of 30°, the transfer rod 100 rotates such, the second handle 60 is rotatable alternately toward and away from the a gear teeth angle of 45°. Consequently, with such a 30° gear teeth angle the user has double the mechanical advantage as he would with a 45° gear teeth angle. Further, the length of the second handle 60 also determines the mechanical advantage of the handles 10,60 over the work elements 40,110.

Figure 4:
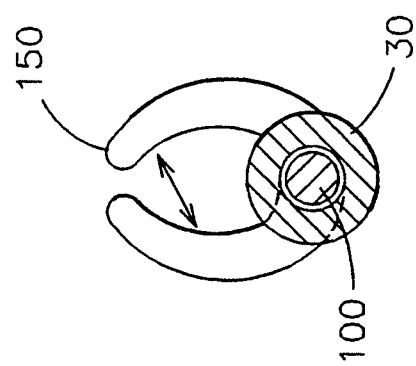
FIG. 4 is a cross-sectional view of the invention, taken along lines 4—4 of FIG. 1, illustrating an embodiment having nips for grasping a workpiece.
Figure 5:
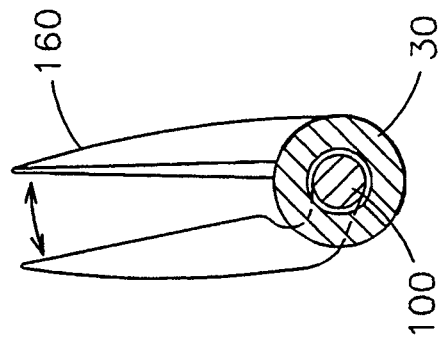
FIG. 5 is similar to FIG. 4 but showing cutting shears for cutting a workpiece.
Figure 6:
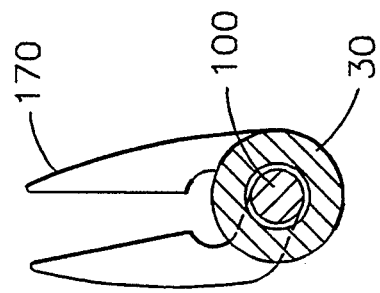
FIG. 6 is similar to FIG. 4 but showing pliers tips for forming a workpiece.

The work elements 40,110 may be mandibles for grasping and manipulating a workpiece therebetween (FIG. 4). Alternatively, the work elements 40,110 may be shears 160 for cutting a workpiece therebetween. Alternatively, the work elements 40,110 may be pliers 170 for holding a workpiece therebetween. In any case, the work elements 40,110 are manufactured from a strong, hardened material, such as steel or other metal.

In an embodiment of the invention that is useful in dentistry, the hollow tube 30 and transfer rod 100 may be of suitable length for positioning the work elements 40,110 inside a person's mouth while an operator's hand that is holding the handles 10,60 is positioned at a distance such that visibility of the work elements 40,110 is not obscured by the hand. As a further advantage over prior art dentistry tools, the present device keeps the hands of the dentist away from the patient's mouth, which may be bleeding or presenting other potentially hazardous materials. Clearly, the length of the hollow tube 30 and of the transfer rod 100 may be of any suitable length for the application at hand. For instance, work performed on an automobile engine may require such length to be several feet.

The work elements 40,110 of the device are preferably positioned so as to face forward of the handles 10,60, thereby extending the reach of the operator. Alternatively, however, the work elements 40,110 may be positioned so as to face toward as the handles 10,60 to enable the work elements 40,110 to approach a workpiece from behind relative to the line of sight of the operator. As such, maximum visibility of the workpiece is provided to the operator since his hands are not positioned so as to block his view of the workpiece. Clearly, the work elements 40,110 may be fashioned to face any other angular position relative to the transfer rod 100.

While the invention has been described with reference to a preferred embodiment, it is to be clearly understood by those skilled in the art that the invention is not limited thereto. Rather, the scope of the invention is to be interpreted only in conjunction with the appended claims.

What is claimed is:

1. A hand tool comprising:
    a first handle providing at one end thereof, a first hinge joint extending away from the handle in a first direction, and a hollow tube extending away from the handle in opposition to the first hinge joint, a fixed work element being attached at a distal end of the tube;
    a second handle aligned with the first handle, and providing a second hinge joint extending in rotational engagement with the first hinge joint and including a first set of gear teeth facing the tube; and;
    a hinge pin pivotally engaged with the first and second hinge joints aligning same, the second handle rotatable alternately toward and away from the first handle about the pin;
    a transfer rod rotatably held within the hollow tube and extending therethrough, a movable work element attached at a distal end thereof adjacent the fixed work element, a toothed gear segment fixed at a proximal end adjacent the second hinge joint and including a second set of gear teeth engaging the first set of gear teeth, whereby as the second handle is rotated about the hinge pin, the first set of gear teeth drive the toothed gear segment to cause the rod to rotate, the movable work element thereby being caused to approach, and alternately retreat, from the fixed work element.

2. The hand tool of claim 1 wherein the work elements are mandibles for grasping and manipulating a workpiece therebetween.

3. The hand tool of claim 1 wherein the work elements are shears for cutting a workpiece therebetween.

4. The hand tool of claim 1 wherein the work elements are pliers tips for holding a workpiece therebetween.

5. The hand tool of claim 1 wherein the hollow tube and transfer rod are of a length such that the work elements may be positioned inside a mouth while a hand holding the handles is positioned at a distance such that visibility of the work elements is not obscured by the hand.

6. The hand tool of claim 1 wherein the work elements are nominally positioned so as to face forward of the handles thereby extending the reach of an operator.

7. The hand tool of claim 1 wherein the work elements are nominally positioned so as to face an operator to enable the work elements to approach a workpiece from behind relative to the line of sight of the operator to provide maximum visibility of the workpiece to the operator.

8. The hand tool of claim 1 wherein the first and second gear teeth each follow a 45 angular degree helical pattern such that action is transferred by 90 degrees between the handles and the work elements.

9. The hand tool of claim 8 wherein the first set of gear teeth is positioned closer to the center of rotation of the pivot pin, than the second set of gear teeth is positioned from the center of rotation of the transfer rod, thereby providing mechanical advantage to the operator.

10. The hand tool of claim 8 wherein the first set of gear teeth is positioned further from the center of rotation of the pivot pin, than the second set of gear teeth is positioned from the center of rotation of the transfer rod, thereby providing a magnification of extent of motion between the handles and the work elements.

* * * * *